United States Patent [19]

Cinco

[11] 4,060,535

[45] Nov. 29, 1977

[54] PROCESS FOR THE PRODUCTION OF METAL SALTS OF ORGANIC ACIDS

[75] Inventor: Salvatore A. Cinco, Succasunna, N.J.

[73] Assignee: Tenneco Chemicals, Inc., Saddle Brook, N.J.

[21] Appl. No.: 719,301

[22] Filed: Aug. 31, 1976

[51] Int. Cl.$^2$ .............................................. C11C 1/00
[52] U.S. Cl. ............................... 260/414; 260/413; 260/429 R; 260/435 R; 260/431; 260/438.1; 260/439 R; 260/515 R; 260/515 A; 260/514 R; 260/520 R; 260/521 R; 260/521 B; 260/526 R; 260/535 P; 260/536; 260/538; 260/539 A; 260/537 R; 260/537 N; 260/540
[58] Field of Search ........... 260/413 S, 515 R, 515 A, 260/414, 429 R, 435 R, 431, 438.1, 439, 518 R, 514 R, 514 B, 520 R, 521 R, 521 B, 526 R, 535 P, 536, 538, 539 A, 537 R, 537 N, 540

[56] References Cited

U.S. PATENT DOCUMENTS

| | | | |
|---|---|---|---|
| 2,681,291 | 6/1954 | Ashley | 260/414 X |
| 2,860,151 | 11/1958 | Lamson et al. | 260/414 X |
| 3,051,571 | 8/1962 | Pergament | 260/413 X |
| 3,476,786 | 11/1969 | Lally et al. | 260/413 S |
| 3,519,571 | 7/1970 | Szczepanek | 260/414 X |
| 3,803,188 | 4/1974 | Scott et al. | 260/414 X |

*Primary Examiner*—Patrick P. Garvin
*Assistant Examiner*—John F. Niebling
*Attorney, Agent, or Firm*—Evelyn Berlow

[57] ABSTRACT

Metal salts of organic acids are produced rapidly and efficiently by subjecting a reaction mixture that contains a metal oxide, hydroxide, or carbonate, an organic acid that has a melting point above 20° C., and a small amount of water to vigorous agitation in an apparatus having attrition and shearing action at a temperature that is below the melting point of the organic acid and below the melting point of the metal salt that is being produced until substantially all of the organic acid has reacted.

10 Claims, No Drawings

PROCESS FOR THE PRODUCTION OF METAL SALTS OF ORGANIC ACIDS

This invention relates to a process for the production of metal salts or organic acids.

Among the processes that have been used for the production of metal salts of organic salts acids are the fusion processes in which a metal oxide, hydroxide, or carbonate is reacted with the appropriate acid at a temperature that is above the melting points of the organic acid and of the metal salt that is being formed. These fusion processes have several disadvantages that limit their use. They require the use of expensive high temperature equipment and complicated handling procedures. Long reaction periods at elevated temperatures are necessary to allow the reaction to go to completion. They yield a discolored molten product that on cooling forms into large lumps. The grinding operation that is required to convert the lumps to the fine powder that is the commercially-acceptable form of the salts often causes serious air pollution problems.

In U.S. Pat. No. 3,476,786, Lally et al, disclosed a process for the production of metal salts that is more economical and easier to carry out than the aforementioned fusion processes. Their process, which yields a dry, finely-divided product, involves grinding a metal oxide, hydroxide, or carbonate with a solid anhydrous fatty acid in the presence of a catalyst, such as anhydrous ammonium carbonate, and in the absence of water at a temperature below the melting point of the metal salt. The salt-forming reaction takes place slowly, and even after a lengthy reaction period the metal salt product contains a substantial amount of unreacted fatty acid.

In accordance with this invention, it has been found that metal salts of organic acids can be prepared rapidly and efficiently by subjecting a reaction mixture that contains a metal components an organic acid component, and a small amount of water to vigorous agitation in an apparatus having attrition and shearing action at a temperature that is below the melting point of the organic acid component and below the melting point of the metal salt that is being produced until substantially all of the organic acid component has reacted. The products obtained, which are light-colored, finely-divided powders, can be used without purification other than drying, when necessary, in the many applications in which metal salts are used.

There are a number of advantages that result from the preparation of metal salts by the process of this invention. This process provides a means of obtaining quantitative yields of high-quality products rapidly and efficiently. It has low energy requirements, and it does not cause the air and water pollution problems that result when metal salts are produced by the previously-known procedures. Because no catalyst or initiator other than water is used, the products are free from contamination by the nitrogenous bases, such as ammonium carbonate, pyridine, and diethanolamine, that have been used by others to catalyze the salt-forming reaction.

In the process of this invention, a metal component, an organic acid component, and water are placed in an apparatus having an attrition and shearing action where they are continually ground at a temperature that is below the melting point of the organic acid component and below the melting point of the metal salt that is being formed until substantially all of the organic acid component has reacted. The temperature may then be allowed to rise to a temperature that is at least 5° C. below the melting point of the product. The product, which may be subjected to subatmospheric pressure at a temperature below its melting point to reduce its water content to the desired level, generally contains not more than 1% by weight of free acid; it preferably contains not more than 0.2% by weight of free acid.

While the reactants may be at any temperature that is below the melting points of the organic acid component and the product at the start of the reaction, they are usually at ambient temperature when the grinding is begun. In those cases in which sufficient heat is evolved by the exothermic reaction or as the result of friction to raise the temperature of the reaction mixture appreciably, external cooling is provided to maintain the reaction temperature in the desired range. To minimize the amount of external cooling that is needed, the reaction is preferably begun at a temperature that is at least 10° C. below the melting points of the organic acid component and the product.

The process can be carried out in any suitable apparatus in which particles of the reactants are continually subdivided under conditions of high shear and attrition at relatively low temperatures and in which external cooling can be provided whenever necessary to maintain the temperature of the reaction mixture in the desired range. The process has been carried out successfully in a Waring Blendor, in a Henschel Fluid Mixer, and in a Littleford Mixer.

The metal components that are used in the production of metal salts by the process of this invention are the oxides, hydroxides, and carbonates of a wide variety of metals including sodium, potassium, lithium, magnesium, calcium, cadmium, strontium, barium, mercury, nickel, cobalt, lead, and copper. A single metal compound or a mixture of two or more of them can be used.

The organic acid components used in the practice of this invention consist of one or more organic acids that melt at temperatures above 20° C. and preferably at temperatures above 30° C. They include saturated and unsaturated aliphatic, aromatic, and alicyclic monocarboxylic, dicarboxylic, and polycarboxylic acids and the anhydrides of these acids. Examples of the useful acids include capric acid, lauric acid, myristic acid, palmitic acid, stearic acid, arachidic acid, behenic acid, melissic acid, monochloroacetic acid, trichloroacetic acid, chloroacrylic acid, hydroxystearic acid, oxalic acid, succinic acid, glutaric acid, adipic acid, azelaic acid, sebacic acid, brassidic acid, erucic acid, petroselic acid, maleic acid, fumaric acid, sorbic acid, citraconic acid, mesaconic acid, itaconic acid, glutaconic acid, malic acid, tartaric acid, citric acid, aconitic acid, tricarballylic acid, tetrolic acid, benzoic acid, m-chlorobenzoic acid, p-chlorobenzoic acid, 2,4-dichlorobenzoic acid, 2,3,6-trichlorobenzoic acid, 2,3,6-tribromobenzoic acid, 2,3,5,6-tetrachlorobenzoic acid, 2,3,5,6-tetrabromobenzoic acid, p-aminobenzoic acid, 3,4-dimethoxybenzoic acid, p-tert.butylbenzoic acid, 2,6-dinitrobenzoic acid, salicyclic acid, p-hydroxybenzoic acid, 2,4-dihydroxybenzoic acid, gallic acid, phenylacetic acid, cinnamic acid, phthalic acid, isophthalic acid, terephthalic acid, trimellitic acid, trimesic acid, cyclohexanecarboxylic acid, cyclopentanecarboxylic acid, cyclopentane-1,2-dicarboxylic acid, abietic acid, and the like. Illustrative of the acid anhydrides that can be used are maleic anhydride, succinic anhydride, glutaric anhydride, cinnamic anhyride, benzoic anhydride, phthalic anhydride, 3- nitrophthalic anhydride, and tetrachlorophthalic anhydride.

The relative amounts of the metal component and the organic acid component that are in the reaction mixture are not critical. Equivalent amounts of the two components or a stoichiometric excess of the metal component is ordinarily used. Particularly good results have been obtained when there was a 5% to 100% molar excess of the metal component in the reaction mixture.

At the start of the reaction, the reaction mixture also contains from 0.1% to 8.0%, based on the total weight of the metal component and the organic acid component, of water, which acts as the initiator for the salt-forming reaction. When less water is added, the reaction takes place too slowly to be commercially acceptable, and it often does not go to completion. The addition of larger amounts of water is usually disadvantageous because the increased time and expense required to dry the product offset the shorter reaction time. The best combination of reaction time and drying time results when from 5.0% to 7.5% by weight of water is added to the reaction mixture to initiate the reaction between the metal component and the organic acid component. In addition to the water that is added to it to initiate the reaction, the reaction mixture contains water that is formed as a by-product of the salt-forming reaction.

When the reaction between the metal component and the organic acid component has been completed, the product may be dried under sub-atmospheric pressure at a temperature below its melting point to reduce its water content to any desired level. The products prepared in this way are light-colored, finely-divided powders that contain not more than 1% by weight of free acid and that meet the commercial specifications that have been established for metal salts of organic salts.

The invention is further illustrated by the following examples.

EXAMPLE 1

A mixture of 800 grams of dry powdered stearic acid, 140 grams of powdered calcium hydroxide, and 50 grams of water was charged to a two-gallon stainless steel vessel equipped with a variable speed, high shear agitator and a thermometer. Agitation of the mixture at the speed of 3600 rpm was begun when the mixture was at 18° C. During the reaction, external cooling was supplied when necessary to remove the heat generated by friction and by the exothermic reaction and to maintain the temperature of the reaction mixture below 60° C. After a 15 minute reaction period, when analysis indicated that substantially all of the stearic acid had reacted, the temperature was allowed to rise to 73° C.

The product, which was obtained in a quantitative yield, was a free-flowing white powder of fine particle size that contained 0.14% by weight of free stearic acid and 4.7% by weight of water. The water content of the calcium stearate was reduced to less than 2% by weight by drying it overnight in a vacuum oven at 50° C.

EXAMPLE 2

The procedure described in Exammple 1 was repeated except that the temperature was maintained between 54° C. and 60° C. throughout the reaction period. The product obtained after a 30 minute reaction period was a free-flowing white powder that contained 0.14% by weight of free stearic acid and 4.7% by weight of water.

An additional 15 minute reaction period at 54°–60° C. did not bring about a further reduction in the stearic acid content or water content of the calcium stearate.

COMPARATIVE EXAMPLE

The procedure described in Example 1 was repeated except that water was not added to the reaction mixture. The product obtained after a 2 hour reaction period contained 5.36% by weight of free stearic acid.

EXAMPLE 3

The procedure described in Example 1 was repeated except that the reaction was carried out in a mixer (Littleford Mixer Model FM 130 D) that contained both mixing plows and a high speed blending chopper. The calcium stearate obtained after a 15 minute reaction period was a finely-divided white powder that melted at 153°–157° C. It contained 0.06% by weight of free stearic acid and 1.4% by weight of water.

EXAMPLE 4

A mixture of 800 grams of dry powdered stearic acid, 91.3 grams of magnesium hydroxide, and 60 grams of water was charged to a two-gallon stainless steel vessel equipped with a variable speed high shear agitator and a thermometer. Agitation of the mixture at the speed of 3600 rpm was begun when the mixture was at 17° C. During the reaction, external cooling was supplied when necessary to maintain the temperature of the reaction mixture below 45° C. After a 15 minute reaction period, when analysis indicated that substantially all of the stearic acid had reacted, the temperature of the reaction product was allowed to rise to 53° C.

The product, which was obtained in a quantitative yield, was a free-flowing white powder that contained 0.8% by weight of free stearic acid.

EXAMPLE 5

The procedure described in Example 4 was repeated except that the temperature was maintained between 40° C. and 45° C. throughout a 45 minute reaction period and then allowed to rise to 53° C. The product was a free-flowing white powder that contained 1.0% by weight of free stearic acid and 8.3% by weight of water. When the magnesium stearate was dried overnight in a vacuum oven at 50° C., its water content was reduced to 3.5%.

EXAMPLE 6

The procedure described in Example 4 was repeated except that the reaction was carried out in a mixer (Littleford Mixer Model FM 130 D) that contained both mixing plows and a high-speed blending chopper. The product obtained after a 15 minute reaction period was a white powder that contained 4.5% by weight of Mg, 3.5% by weight of water, 0.13% by weight of free stearic acid, and an undetectable amount of water-soluble salts.

EXAMPLE 7

A series of metal salts was prepared by mixing a metal component, an organic acid component, and water in a Waring Blendor at ambient temperature for 10–15 minutes. The products were dried overnight in a vacuum oven at 50° C.

The metal components and organic acids and the amounts of each that were used, the amounts of water that were added, and the analyses of the products are set forth in the Table.

All of the products met or surpassed the commercial specifications that have been established for these metal salts.

TABLE

| Ex. No. | Metal Salt | Reactants | | | Analysis of Product (% by weight) | | | |
|---|---|---|---|---|---|---|---|---|
| | | Metal Component (grams) | Organic Acid Component (grams) | Water Added (grams) | Free Acid | Water | Metal | Ash |
| 7A | Sodium Stearate | 50% NaOH (20.6 grams) | Stearic Acid (67.6 grams) | — | 0.12 | 0.04 | — | 17.3 ($Na_2CO_3$) |
| 7B | Sodium Stearate | 97% NaOH (10.3 grams) | Stearic Acid (67.3 grams) | 1 | 0.39 | <0.1 | — | 17.1 ($Na_2CO_3$) |
| 7C | Normal Lead Stearate | PbO (30.0 grams) | Stearic Acid (67.3 grams) | 5 | 0.13 | 0.10 | — | 30.9 (PbO) |
| 7D | Sodium Benzoate* | $Na_2CO_3$(anh.) (27.0 grams) | Benzoic Acid (61.0 grams) | 4 | 2.0 | 0.9 | — | — |
| 7E | Sodium Benzoate | 97% NaOH (20.6 grams) | Benzoic Acid (61.0 grams) | 1 | <0.1 | 0.3 | — | — |
| 7F | Sodium Salicylate | 97% NaOH (20.0 grams) | Salicylic Acid (69.0 grams) | 1 | <0.1 | <0.1 | — | — |
| 7G | Dibasic Lead Phthalate* | PbO (134.0 grams) | Phthalic Anhydride (29.6 grams) | 2 | 5.8 | 4.0 | 74.8 Pb | — |
| 7H | Cadmium Benzoate | $Cd(OH)_2$ (43.1 grams) | Benzoic Acid (61.1 grams) | 2 | 1.0 | 3.9 | 31.9 Cd | — |
| 7I | Barium-Cadmium Stearate | $Ba(OH)_2 \cdot H_2O$ (27.3 grams) $Cd(OH)_2$ (13.2 grams) | Stearic Acid (108.8 grams) | 3 | 0.8 | 0.3 | 14.2 Ba 6.5 Cd | — |

*When the reaction was carried out at ambient temperature for 30 minutes, the product contained less than 1% of free acid.

What is claimed is:

1. The process for the production of finely-divided metal salts of carboxylic acids that comprises the steps of
    a. forming a reaction mixture that consists essentially of
        1. a metal component selected from the group consisting of the oxides, hydroxides, and carbonates of the alkali metals, magnesium, calcium, cadmium, strontium, barium, mercury, nickel, cobalt, lead, copper, and mixtures thereof,
        2. a carbxylic acid component having a melting point above 20° C., and
        3. from 0.1% to 8.0%, based on the total weight of the metal component and the carboxylic acid component, of water and
    b. subjecting said reaction mixture to vigorous agitation in an apparatus having an attrition and shearing action at a temperature that is below the melting point of the carboxylic acid component and below the melting point of the metal salt that is being produced until substantially all of the carboxylic acid component has reacted.

2. The process of claim 1 wherein the reaction mixture formed in Step a) contains from 5.0% to 7.5% by weight of water.

3. The process of claim 1 wherein the carboxylic acid component of the reaction mixture formed in Step a) has a melting point above 30° C.

4. The process of claim 1 wherein in Step b) the reaction mixture is subjected to vigorous agitation while at a temperature that is at least 10° C. below the melting point of the carboxylic acid component and the melting point of the metal salt that is being produced.

5. The process of claim 1 wherein in Step b) the reaction mixture is subjected to vigorous agitation until the metal salt that is being produced contains not more than 1% by weight of free acid.

6. The process of claim 1 wherein in Step b) the reaction mixture is subjected to vigorous agitation until the metal salt that is being produced contains not more than 0.2% by weight of free acid.

7. The process of claim 1 wherein the carboxylic acid component of the reaction mixture formed in Step a) comprises stearic acid.

8. The process of claim 1 wherein the carboxylic acid component of the reaction mixture formed in Step a) comprises benzoic acid.

9. The process of claim 1 wherein the metal component of the reaction mixture formed in Step a) comprises calcium hydroxide.

10. The process of claim 1 wherein the metal component of the reaction mixture formed in Step a) comprises cadmium hydroxide.

* * * * *

UNITED STATES PATENT AND TRADEMARK OFFICE
CERTIFICATE OF CORRECTION

PATENT NO. : 4,060,535
DATED : Nov. 29, 1977
INVENTOR(S) : Salvatore A. Cinco

It is certified that error appears in the above-identified patent and that said Letters Patent are hereby corrected as shown below:

Column 1, line 23, after "al" change the comma to a period.

Column 1, line 39, change "components" to -- component, --.

Column 3, line 62, change "Exammple" to -- Example --.

Column 5, line 42, change "carbxylic" to -- carboxylic --.

Signed and Sealed this

Fourteenth Day of March 1978

[SEAL]

Attest:

RUTH C. MASON
Attesting Officer

LUTRELLE F. PARKER
Acting Commissioner of Patents and Trademarks